United States Patent
Duprat et al.

(10) Patent No.: US 9,855,244 B2
(45) Date of Patent: *Jan. 2, 2018

(54) O/W-EMULSION-TYPE TOPICAL PHARMACEUTICAL COMPOSITIONS CONTAINING A RETINOID

(71) Applicant: GALDERMA RESEARCH & DEVELOPMENT, Biot (FR)

(72) Inventors: Agnès Duprat, Mougins (FR); Claire Mallard, Mougins (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/404,877

(22) PCT Filed: May 30, 2013

(86) PCT No.: PCT/EP2013/061199
§ 371 (c)(1),
(2) Date: Dec. 1, 2014

(87) PCT Pub. No.: WO2013/178758
PCT Pub. Date: Dec. 5, 2013

(65) Prior Publication Data
US 2015/0148400 A1 May 28, 2015

Related U.S. Application Data

(60) Provisional application No. 61/654,694, filed on Jun. 1, 2012.

(30) Foreign Application Priority Data

Jun. 1, 2012 (FR) .................................... 12 55091

(51) Int. Cl.
| | | |
|---|---|---|
| A61K 31/402 | (2006.01) |
| A61K 9/00 | (2006.01) |
| A61K 47/26 | (2006.01) |
| A61K 9/107 | (2006.01) |
| A61K 31/40 | (2006.01) |
| A61K 47/06 | (2006.01) |
| A61K 47/10 | (2017.01) |

(52) U.S. Cl.
CPC .......... *A61K 31/402* (2013.01); *A61K 9/0014* (2013.01); *A61K 9/107* (2013.01); *A61K 31/40* (2013.01); *A61K 47/06* (2013.01); *A61K 47/10* (2013.01); *A61K 47/26* (2013.01)

(58) Field of Classification Search
CPC .................................................... A61K 31/402
See application file for complete search history.

(56) References Cited

U.S. PATENT DOCUMENTS

| | | | | |
|---|---|---|---|---|
| 5,658,575 A | * | 8/1997 | Ribier | A61K 8/0295 424/401 |
| 5,919,487 A | * | 7/1999 | Simonnet | A61K 8/11 424/47 |
| 2003/0170295 A1 | * | 9/2003 | Kim | A61K 9/7061 424/449 |
| 2004/0213754 A1 | * | 10/2004 | Cole | A61K 8/41 424/70.27 |
| 2007/0043119 A1 | * | 2/2007 | Graeber | A61K 9/0014 514/569 |

FOREIGN PATENT DOCUMENTS

| | | |
|---|---|---|
| EP | 0780115 A1 | 6/1997 |
| WO | 2006/066978 A1 | 6/2006 |
| WO | 2007/039057 A1 | 4/2007 |
| WO | 2008/148968 A1 | 12/2008 |

OTHER PUBLICATIONS

English Translation of International Search Report dated Jul. 3, 2013 corresponding to International Patent Application PCT/EP2013/061199, 2 pages.

* cited by examiner

*Primary Examiner* — Matthew Coughlin
(74) *Attorney, Agent, or Firm* — Dentons US LLP

(57) ABSTRACT

O/W-emulsion-type topical pharmaceutical compositions including a retinoid are described. Also described, is a topical pharmaceutical composition including by way of an active pharmaceutical ingredient, a retinoid in a physiologically acceptable composition. Preparation methods and the use of the same in dermatology are also described.

33 Claims, 2 Drawing Sheets

O/W-EMULSION-TYPE TOPICAL PHARMACEUTICAL COMPOSITIONS CONTAINING A RETINOID

CROSS-REFERENCE TO RELATED APPLICATIONS

This application is a National Stage of PCT/EP2013/061199, filed May 30, 3013, and designating the United States (published Dec. 5, 2013, as WO 2013/178758 A1), which claims priority under 35 U.S.C. §119 to U.S. Provisional Application No. 61/654,694, filed Jun. 1, 2012, and French Patent Application No. 1255091, filed Jun. 1, 2012, each hereby expressly incorporated by reference in its entirety and each assigned to the assignee hereof.

BACKGROUND OF THE INVENTION

The invention relates to a topical pharmaceutical composition comprising as pharmaceutical active agent a retinoid in a physiologically acceptable medium, to the method for the preparation thereof and to the use thereof in dermatology.

In the field of dermatology and of the formulation of pharmaceutical compositions, those skilled in the art are led to use compositions that must be physically and chemically stable. They must also allow the release of the active agent and promote its penetration into the skin layers in order to improve its efficacy.

The horny layer or stratum corneum is the most superficial part of the epidermis. Conventionally likened to a wall of "bricks and mortar", it consists of dead cells, corneocytes, embedded in inter-corneocyte lipids. The stratum corneum lies on the epidermis which is the first viable layer of the skin. It contains numerous cell types and is avascular. Finally, the dermis consists of a small number of cells, numerous proteins which provide support for the tissue, and a vascular network. While the stratum corneum is principally lipophilic in nature owing to the presence of the inter-corneocyte lipids, the epidermis and the dermis are principally hydrophilic in nature, the presence of vessels in the dermis additionally providing clearance of this compartment.

It is commonly accepted that the mechanisms of cutaneous penetration and permeation are dependent, on the one hand, on the coefficients of partition of the compounds between the vehicle applied and the various compartments of the skin (stratum corneum, epidermis then vascular dermis) and, on the other hand, on the coefficient of diffusion of these compounds in each layer of the skin. Depending on their physicochemical characteristics, in particular their lipophilic nature, certain compounds exhibit a high affinity and a high coefficient of diffusion in the stratum; they are therefore stored in the stratum, and to a lesser extent in the epidermis. On the other hand, their partition in the dermis, which is vascularized, and which is more hydrophilic in nature than the epidermis or the stratum, will be low. In this case, the upper layers of the skin, and in particular the stratum, then constitute an actual reservoir for the accumulation of the pharmaceutical active agent. Typically, the penetration kinetics of such compounds exhibit, over time, an increase in the amount of active agent in the stratum, and to a lesser extent in the epidermis, followed by a plateau during which this amount no longer varies. The state of equilibrium between the penetration of the active agent into the compartment and its clearance is then reached.

In certain cases, it is important to be able to modulate these typical kinetics in such a way that the pharmaceutical active agent can penetrate weakly into the skin in a prolonged and controlled manner. This type of penetration and accumulation in the skin can then be similar to zero order kinetics, with reference to the zero order linear kinetics of diffusion and transcutaneous permeation observed for certain pharmaceutical preparations applied to a membrane or to skin.

The active molecules, the passage of which to their target is sought, are rarely isolated; they are usually in a more or less complex formulation which, as appropriate, may be a cream, an ointment, a lotion, a powder or a gel.

After the phase of contact between the molecule and the surface of the skin, the active substance will have to leave its vehicle in order to penetrate into the horny layer, with more or less ease.

Generally, topical pharmaceutical compositions such as gels, creams, lotions or solutions release the active ingredient(s) by diffusion directly proportional to the concentration gradient in the composition.

In other words, after application to the skin, the active ingredient(s) is (are) released relatively immediately and then the release kinetics tend toward zero to obtain a plateau. The active ingredient(s) is (are) then no longer absorbed on the skin.

In order to obtain release kinetics independent of the concentration gradient, there are several types of topical formulations, such as:
- the formulation of supersaturated solutions, i.e. compositions in which the active ingredient(s) is (are) in very concentrated solution,
- the production of patches in which the release of the active ingredient(s) is controlled by a membrane, which is permeable and generally adhesive, directly in contact with the skin.

Supersaturated solutions are very often unstable and do not make it possible to obtain good physical stability of the composition which may be a gel, a cream, a lotion or an ointment. Patches are, on the other hand, more stable, but have the drawback of a more complex processing with an application surface area limited by the size of the patch.

SUMMARY

The problem that the present invention proposes to solve herein is thus that of designing a pharmaceutical composition of oil-in-water emulsion type, which is physically and chemically stable, comprising at least one active ingredient, such as one or more retinoids, having a nonconventional release profile. It must also be easy to use and of acceptable cosmeticity for application to any area of the body that may be affected by the pathological condition.

There is thus a need to have a topical pharmaceutical composition that can satisfy one or more of the following aspects:
- of obtaining good physical stability without any risk of crystallization of the active ingredient(s),
- of allowing well-tolerated applications without surface area limitation,
- of obtaining gradual penetration of the active ingredient(s) at the level of the target thereof.

The applicant is thus seeking to improve these parameters by the present invention.

DETAILED DESCRIPTION

Figure 1:
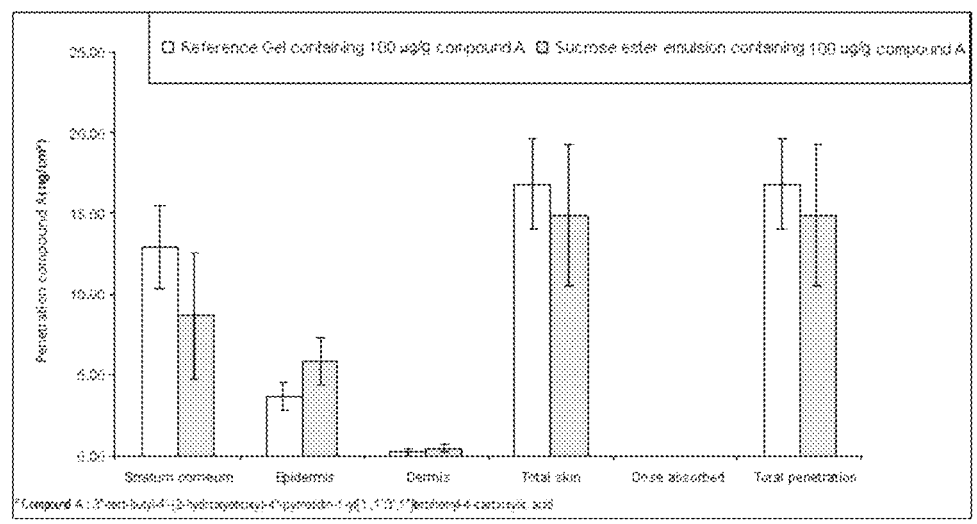
FIG. 1 is the distribution profile of two formulations containing compound A in the various skin compartments.

The term "chemical stability" is intended to mean in particular stability of the active ingredient. The term "physical stability" is intended to mean in particular an absence of crystallization or precipitation of the active agent, or an absence of phase separation or of modification of its color within the composition.

A physically stable composition according to the invention is consequently a composition that does not present any macroscopic change of appearance (phase separation, change of color, of appearance, etc.) or microscopic change of appearance (recrystallization of the active agents) after storage at temperatures of 25° C., 4° C. and 40° C., for 1 month, 2 months, 3 months and 6 months.

A chemically stable composition according to the invention is, consequently, a composition in which the content of active ingredient remains stable after six months at ambient temperature (AT) and at 40° C. A stable content of active ingredient means according to the invention that the content shows very little variation relative to the initial content, i.e. that the variation in the content of active ingredient at time T should not be less than 90% and more particularly than 95% of the initial content at T0.

Other parameters should also be taken into account by those skilled in the art for the choice of ingredients of a pharmaceutical composition. Specifically, the pharmaceutical composition that may be used according to the invention as a medicament will also have to be formulated in accordance with the pathological condition to be treated.

By way of nonlimiting example, a composition for treating acne will need to be of non-greasy cosmetic appearance, whereas a composition for treating ichthyosis, ichthyosiform conditions, palmoplantar hyperkeratosis or psoriasis will need to be emollient and moisturizing, and may be richer in fatty substances, while at the same time avoiding the non-cosmetic greasy appearance.

In the present invention, the applicant has shown, surprisingly, that it is possible to obtain a composition of oil-in-water emulsion type, containing a retinoid, which is physically and chemically stable, and which has zero order active agent penetration kinetics.

The term "composition which has zero order penetration kinetics" is intended to mean a composition which, once applied to the surface of the skin, has a profile of gradual and controlled penetration of the active agent at the level of the target thereof.

As a nonlimiting example, the target of the retinoid is more particularly at the level of the epidermis for the treatment of acne, ichthyosis, ichthyosiform conditions, palmoplantar keratosis and psoriasis.

The term "solubilized form of the active agent" is intended to mean a dispersion of the active agent in the molecular state in a liquid, no crystallization of the active agent being visible to the naked eye or even under a cross-polarized optical microscope.

3"-Tert-butyl-4'-(2-hydroxyethoxy)-4"-pyrrolidin-1-yl[1,1';3',1"]terphenyl-4-carboxylic acid (called Compound A in the rest of the text) belongs to the family of retinoids which are RAR-gamma receptor agonists. Since RAR-gamma receptors are located in the epidermis, it is important for the release of the retinoid to take place in this part of the skin in order to have a clinical efficacy. The release profile of this type of molecule in the skin is very important for reaching the site of activity and obtaining optimum efficacy.

Knowing the physicochemical characteristics of the active agent, the applicant has had to face a certain number of constraints regarding the use of Compound A:

Compound A has low solubility in the solvents customarily used in the fatty phases of topical emulsions, Compound A chemically degrades in many of its solvents, Compound A chemically degrades in the presence of many emulsifiers.

It is not therefore simple to have good chemical stability of Compound A when it is solubilized or in the presence of the emulsifiers.

In order to produce an oil-in-water (O/W) emulsion according to the invention, pre-formulation studies were carried out in order to reveal the excipients enabling good solubilization and also good stability of the active agent.

Stability of Compound A in its Principal Oily Solvents (Determined by HPLC)

| | Excipients | Compound A | |
|---|---|---|---|
| Trade Name | INCI name | % | Stability results |
| Miglyol 812N | Caprylic/capric triglycerides | 0.005% | Stable/Ok 6 Months 40° C. |
| Sweet almond oil | *Prunus Amygdalus Dulcis* (Sweet Almond) Oil | 0.005% | Stable/Ok 6 Months 40° C. |
| Capryol 90 | Propylene glycol monocaprylate | 0.05% | Stable/Ok 6 Months 40° C. |
| Arlacel 83V Pharma | Sorbitan Sesquioleate | 0.05% | Stable/Ok 6 Months 40° C. |
| Lauroglycol FCC | Propylene glycol laurate | 0.05% | Stable/Ok 6 Months 40° C. |
| Arlamol E | PPG-15 stearyl ether | 0.05% | Stable/Ok 6 Months 40° C. |
| Phenoxetol | Phenoxyethanol | 0.05% | Stable/Ok 6 Months 40° C. |
| Labrafil M1944CS | Apricot Kernel Oil PEG-6 Ester | 0.05% | Stable/Ok 6 Months 40° C. |
| Dipropylene Glycol Care | Dipropylene glycol | 0.05% | Unstable |
| Brij 30 | Laureth-4 | 0.05% | Unstable |
| Benzyl alcohol | Benzyl Alcohol | 0.05% | Unstable |
| Eutanol G | Octyldodecanol | 0.05% | Unstable |

-continued

| Excipients | | Compound A | |
|---|---|---|---|
| Trade Name | INCI name | % | Stability results |
| Myritol PC | Propylene glycol dicaprylate/dicaprate | 0.05% | Unstable |
| Arlasolve DMI | Dimethyl Isosorbide | 0.05% | Unstable |

The limits set for good stability are 95%-105% as relative percentage with respect to T0.

These studies of stability of Compound A in its principal solvents show that Compound A chemically degrades in many of its solvents (chemical instability).

The results of this study allowed us to select the principal solvent of the active agent and the cosolvent oils among the solvents exhibiting good stability results, with the objective of developing O/W emulsions in which the active agent is solubilized in the oily phase.

(3) Stability of Compound A in Mixtures of Excipients (Solvent/Surfactants), Determined by HPLC:

Studies of the stability of Compound A solubilized in solvent oils in which it is stable, as previously demonstrated, in the presence of surfactants were carried out:

| Mixture of excipients | | Compound A | Stability |
|---|---|---|---|
| Trade Name | INCI name | % | results |
| Cremophor EL/Labrafil M1944CS | PEG-35 Castor Oil/Apricot Kernel Oil PEG-6 Ester | 0.05% | Unstable |
| Tween 80/Arlamol E | Polysorbate-80/PPG-15 stearyl ether | 0.05% | Unstable |
| Cremophor EL/Lauroglycol FCC | PEG-35 Castor Oil/Propylene glycol laurate | 0.05% | Unstable |
| Tween 80/Hexylene glycol | Polysorbate-80/Hexylene glycol | 0.2% | Unstable |
| Cremophor EL/Labrafil M1944CS | PEG-35 Castor Oil/Apricot Kernel Oil PEG-6 Ester | 0.2% | Unstable |
| Tween 80/Lauroglycol FCC | Polysorbate-80/Propylene glycol laurate | 0.2% | Unstable |
| Arlacel 165/Lauroglycol FCC | Glyceryl stearate PEG-100 Stearate/Propylene glycol laurate | 0.05% | Unstable |
| GlucateSS-Glucamate SSE-20/Arlamol E | Methyl Glucose Sesquistearate-PEG-20 Methyl Glucose Sesquistearate/PPG-15 stearyl ether | 0.05% | Unstable |

The limits set for good stability are 95%-105% as relative percentage with respect to T0. These studies showed that Compound A chemically degrades in the presence of many surfactants conventionally used in emulsions of oil-in-water (O/W) type.

The aim of the present invention is the development of pharmaceutical compositions containing a retinoid in the form of emulsions of O/W (oil-in-water) type based on emulsifiers of sucrose ester type, in which the active agent is solubilized in the fatty phase. In these pharmaceutical compositions, the retinoid exhibits good physical and chemical stability. In these compositions, the retinoid gradually penetrates at the level of its target.

The applicant has discovered that, when Compound A is solubilized with solvents and cosolvents in which it is stable and when sucrose esters are used as emulsifiers, the compositions according to the invention are stable for at least 6 months at ambient temperature and at +40° C.

A subject of the present invention is a topical pharmaceutical composition of oil-in-water emulsion type comprising a lipophilic phase and one or more surfactants and which is in the form of a pre-concentrate which, after dilution with an aqueous phase, makes it possible to obtain micro and submicronic emulsions.

The constituents of the fatty phase must be chosen so as to be a solvent of the active agent and can be combined with other oils or fatty substances in order to prepare a composition having desired properties.

The composition according to the invention thus relates to a topical composition of oil-in-water emulsion type, comprising:

a fatty phase containing at least one active ingredient chosen from retinoids, at least one principal solvent of the active agent, one or more cosolvent oils, and a mineral oil, an aqueous phase containing at least one surfactant of the sucrose ester family, at least one polyol and purified water.

For the purposes of the present invention, the term "retinoid" is intended to mean a hydrophobic retinoid such as the compounds protected in patent application WO2006/066978, such as 3"-tert-butyl-4'-(2-hydroxyethoxy)-4"-pyrrolidin-1-yl[1,1';3',1"]terphenyl-4-carboxylic acid.

The composition according to the invention thus relates to a topical composition of oil-in-water emulsion type, comprising:

a fatty phase containing 3"-tert-butyl-4'-(2-hydroxyethoxy)-4"-pyrrolidin-1-yl[1,1';3',1"]terphenyl-4-carboxylic acid, at least one principal solvent of the active agent, one or more cosolvent oils, and a mineral oil, an aqueous phase containing at least one surfactant of the sucrose ester family, at least one polyol and at least 5% by weight of water.

According to one preferred mode, the composition according to the invention relates to a topical composition of oil-in-water emulsion type comprising:

a fatty phase containing at least one active ingredient chosen from retinoids, at least one principal solvent of the active agent, one or more cosolvent oils, and a mineral oil, an aqueous phase containing at least one surfactant of the sucrose ester family, at least one polyol, at least one gelling agent and at least 5% by weight of water.

The term "gelling agent" is intended to mean a polymer compound capable of conferring on the composition the texture of a gel. They may be gelling agents of vegetable origin, gums, pectins, celluloses and their derivatives, gelling agents of microbiological origin, such as xanthan gum, or gelling agents of synthetic origin.

In one particularly preferred mode, the composition is in emulsion form and comprises:

a fatty phase comprising between 0.00001% and 1% of at least one retinoid, an aqueous phase comprising from 0.1% to 15% of sucrose esters, from 1% to 40% of polyol, from 0.005% to 10% of hydrophilic gelling agent and at least 5% of water, from 0 to 15% of one or more additives.

According to one particular mode of the invention, the composition is composed of:

a fatty phase comprising from 0.00001% to 1% of at least one retinoid; from 0.1% to 10% of principal solvent of the retinoid; from 0.5% to 60% of oils which are cosolvents of the retinoid; from 0.5% to 20% of mineral oils; from 0.1% to 10%, preferably from 0.5% to 3% of fatty-phase thickener; from 0 to 20% of silicone oil;

an aqueous phase comprising from 0.1% to 15% of emulsifiers of the sucrose ester family; from 1% to 40%, preferably from 4% to 10% of polyol; from 0.005% to 10% of aqueous-phase gelling agent;

from 0.01% to 5% of preserving system;

and from 0 to 15%, preferably from 0.1% to 10% of additives.

According to one particular mode of the invention, the composition more particularly suitable for the treatment of acne is composed:

of a fatty phase comprising from 0.00001% to 1% of 3"-tert-butyl-4'-(2-hydroxyethoxy)-4"-pyrrolidin-1-yl [1,1';3',1"]terphenyl-4-carboxylic acid (compound A); from 0.2% to 5% of principal solvent of compound A; from 0.5% to 60% of oils which are cosolvents of compound A; from 0.5% to 20% of mineral oils; from 0.1% to 10% of fatty-phase thickener; from 0 to 20% of silicone oil;

of an aqueous phase comprising from 0.1% to 15% of emulsifiers of the sucrose ester family; from 1% to 40% of polyol; from 0.005% to 10% of aqueous-phase gelling agent;

from 0.01% to 5% of preserving system;

and of from 0.001% to 15% of additives.

In the case of pharmaceutical compositions suitable for the treatment of acne, the fatty phase is preferably composed of:

0.00001% to 1% of at least one retinoid;
1% of phenoxyethanol;
1.980% of cetearyl alcohol;
3% of mineral oils;
and 15% to 22% of cosolvent oils.

In one particular mode of the invention, the composition more particularly suitable for the treatment of ichthyosis, ichthyosiform conditions, palmoplantar hyperkeratosis or psoriasis is composed:

of a fatty phase comprising from 0.00001% to 1% of 3"-tert-butyl-4'-(2-hydroxyethoxy)-4"-pyrrolidin-1-yl [1,1';3',1"]terphenyl-4-carboxylic acid (compound A); from 0.2% to 5% of solvent of compound A; from 0.5% to 60% of oils which are cosolvents of compound A; from 0.5% to 20% of mineral oils; from 0.1% to 10% of fatty-phase thickener; from 0 to 20% of silicone oil;

of an aqueous phase comprising from 0.1% to 15% of emulsifiers of the sucrose ester family; from 1% to 40% of polyol; from 0.005% to 10% of aqueous-phase gelling agent;

of from 0.01% to 5% of preserving system;

and of from 0.001% to 15% of additives.

The surfactant system comprises at least one principal surfactant chosen from the sucrose ester category, such as sucrose stearate and sucrose palmitate. This or these sucrose ester(s) can be combined with any other surfactant capable of acting as a co-surfactant.

The aqueous phase can contain, in a nonlimiting manner, one or more polyols, one or more hydrophilic-phase gelling agents, and various types of additives.

The % are expressed by weight relative to the total weight of the composition, unless specifically mentioned.

In the invention, the compositions contain 3"-tert-butyl-4'-(2-hydroxyethoxy)-4"-pyrrolidin-1-yl[1,1';3',1"]terphenyl-4-carboxylic acid, called Compound A, at concentrations ranging from 0.00001% to 1% and preferentially from 0.0001% to 0.1% by weight relative to the total weight of the composition.

As previously indicated, the aqueous phase contains at least one surfactant of the sucrose ester family.

In the invention, the compositions contain surfactants of sucrose ester type which have been chosen by the applicant for their good compatibility with Compound A, but also because they make it possible to produce very fine emulsions which have very smooth textures and excellent skin tolerance.

Sucrose esters are nonionic surfactants comprising a hydrophilic group consisting of the sucrose part and a lipophilic group consisting of a fatty acid. As sucrose generally has a total of 8 hydroxyl groups, it is thus possible to obtain sucrose esters ranging from a sucrose "monoester" to a sucrose "octaester". "Sucrose esters" are esters of fatty acids and of sucrose, sucrose being a disaccharide composed of glucose and fructose. The term "sucrose ester" is intended to mean, by way of nonlimiting example, the sucrose myristate sold under the name Surfhope C-1416 supplied by Gattefosse, sucrose palmitate sold under the name Surfhope C-1615, Surfhope C-1616 and Surfhope SE Pharma D-1616 supplied by Gattefosse, but also sold under the name Sisterna PS750-C and supplied by Unipex, and sucrose stearate sold under the name Surfhope C-1811, Surfhope SE Pharma D-1816, Surfhope C-1815 and Surfhope C-1816 supplied by Gattefosse, but also sold under the name Sisterna SP50-C and Sisterna SP70-C and supplied by Unipex.

In one preferred mode according to the invention, the composition comprises sucrose palmitate or sucrose stearate or a mixture thereof in a concentration ranging from 0.1% to 15% and preferentially from 0.5% to 5% by weight relative to the total weight of the composition.

The fatty phase according to the invention should be chosen so as to contain at least one principal solvent of compound A, one or more cosolvent oils, and a mineral oil.

The term "principal solvent" is intended to mean a liquid which has the property of dissolving, diluting or extracting other substances without causing chemical modification of these substances and without itself being modified.

According to the invention, a principal solvent is such a liquid, in which the retinoids (more preferentially compound A) have a solubility, at ambient temperature and atmospheric pressure, greater than or equal to 0.1% by weight.

Preferentially, the principal solvent is present in a concentration ranging from 0.1% to 10%.

In the case where the active agent of the composition according to the invention is Compound A, the principal solvent may be, for example, the phenoxyethanol sold under the name phenoxetol by Clariant, present in a concentration ranging from 0.2% to 5% and preferentially from 0.5% to 2%.

The term "cosolvent" is intended to mean a substance which acts as a solvent in combination with another substance.

The fatty phase of the invention also comprises:
one or more cosolvent oils, preferentially the following cosolvent oils: caprylic/capric triglycerides (Miglyol 812N) supplied by IMCD, Prunus Amygdalus Dulcis (sweet almond) oil supplied by Sictia, propylene glycol monocaprylate (Capryol 90) supplied by Gattefosse, propylene glycol laurate (Lauroglycol FCC) supplied by Gattefosse, PPG-15 stearyl ether (Arlamol PS15E-LQ) supplied by Croda, sorbitan sesquioleate (Arlacel 83VPharma) supplied by Croda, apricot kernel oil PEG-6 ester (Labrafil M1944CS) supplied by Gattefosse, refined coconut oil supplied by Olvea at contents ranging from 0.5% to 60% and preferentially from 10% to 20% for the acne indication and between 20% and 40% for the ichthyosis, palmoplantar hyperkeratosis and psoriasis indications,
one or more mineral oils, for instance liquid paraffins of different viscosities, for instance Marcol 152, Marcol 52 or Primol 352 sold by Univar, at contents ranging from 0.5% to 20% and preferentially from 2% to 6%.

Other oils or fatty substances may be added to the fatty phase of the composition in a varied manner by those skilled in the art in order to prepare a composition having the desired properties, for example in terms of consistency or texture.

The composition according to the invention may also contain, for example:
one or more silicone oils for improving the properties of the formula on application, such as cyclomethicone (St-Cyclomethicone 5NF) or dimethicone (Q7 9120 silicon fluid having a viscosity of 20 cst to 12 500 cst from Dow Corning) between 0 and 20% and preferentially between 0 and 6%,
one or more fatty-phase thickeners of fatty alcohol type, such as cetyl alcohol (Crodacol C70 supplied by Croda/Kolliwax CA supplied by BASF), cetearyl alcohol (Crodacol 1618 supplied by Croda, Tego Alkanol 1618 supplied by Evonik, but also Kolliwax CSA 50), stearyl alcohol (Crodacol S95 supplied by Croda, Kolliwax SA supplied by BASF, Tego Alkanol 18 supplied by Evonik), but also behenyl alcohol (Nacol 22-98 supplied by Sasol, but also Behenyl Alcohol 65 80 supplied by Nikko Chems), or of carnauba wax type supplied by Baerlocher, but also the beeswax sold under the name Cerabeil Blanchie Dab supplied by Univar between 0.1% and 10% and preferentially between 0.5% and 6%.

Thus, the fatty phase of the emulsion according to the invention may be present in a content of between 1% and 95% by weight relative to the total weight of the composition, preferably between 5% and 85% and more preferentially between 15% and 50% by weight relative to the total weight of the composition.

The good chemical and physical stabilities of the composition according to the invention are obtained in particular via the choice of the surfactants. Thus, the composition according to the invention also comprises at least one principal surfactant chosen from the category of sucrose esters.

As the composition according to the invention is an oil-in-water emulsion, it comprises an aqueous phase containing at least 5% of water relative to the total weight of the composition, preferably between 5% and 90%.

In one preferred mode according to the invention, the aqueous phase also contains a polyol (minimum a triol), preferably selected from glycerin, diglycerin or sorbitol (Neosorb supplied by Roquette, Parteck SI supplied by Merck, but also Sorbitol USP Powder supplied by Lipo Chemicals) and the amount of which is between 1% and 40% by weight relative to the total weight of the composition and preferentially between 4% and 10% for the acne indication and between 10% and 25% for the ichthyosis, palmoplantar hyperkeratosis and psoriasis indications.

In one preferred mode, the composition according to the invention contains glycerin in a content of between 1% and 20% and a proportion of water of between 5% and 90%.

In one embodiment, the composition according to the invention also comprises one or more hydrophilic-phase gelling agents. As nonlimiting examples of gelling agents that may be included in the compositions according to the invention, mention may be made of the acrylates/C10-30 alkyl acrylate crosspolymer sold under the name Pemulen TR1 or Pemulen TR2 by the company Lubrizol, the carbomers sold under the name Ultrez 20®, Ultrez 10®, Carbopol 1382® or Carbopol ETD2020NF®, Carbopol 981 or Carbopol 980 by the company Lubrizol, polysaccharides, non-limiting examples being xanthan gum such as Xantural 180® sold by the company Kelco or Satiaxane UCX 911 sold by Cargill, polyvinyl alcohol such as Polyvinyl alcohol 40-88 sold by Merck, gellan gum sold under the name Kelcogel by the company Kelco, guar gum, cellulose and derivatives thereof such as microcrystalline cellulose and sodium carboxymethylcellulose sold under the name Avicel CL-611 by the company FMC Biopolymer, hydroxypropylmethylcellulose, in particular the product sold under the name Methocel E4M premium by the company Dow Chemical, or hydroxyethylcellulose, in particular the product sold under the name Natrosol HHX 250® by the company Ashland, the family of aluminum magnesium silicates such as Veegum K sold by the company Vanderbilt, the family of acrylic polymers coupled to hydrophobic chains such as PEG-150/decyl/SMDI copolymer sold under the name Aculyn 44 (polycondensate comprising at least, as elements, a polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%), the family of modified starches such as the modified potato starch sold under the name Structure Solanace, or mixtures thereof, and gelling agents of the family of polyacrylamides, such as the mixture sodium acryloyldimethyltaurate copolymer/isohexadecane/polysorbate 80 sold under the name Sepineo P600® (or Simulgel 600 PHA®) by the company SEPPIC, the mixture polyacrylamide/isoparaffin C13-14/laureth-7, for instance the product sold under the name Sepigel 305 by the company SEPPIC, the family of carrageenans, in particular divided into four major families: κ, λ, β, ω such as the Viscarin® products and the Gelcarin® products sold by the company IMCD.

Preferentially, use will be made of gelling agents of polyacrylamide type, such as sodium acryloyldimethyltaurate copolymer/isohexadecane/polysorbate 80, for their good compatibility with the active ingredient and their good ability to stabilize emulsions, at preferential concentrations ranging from 0.005% to 10% and more preferentially from 0.5% to 4%.

In one particularly preferred embodiment, the composition according to the invention also comprises one or more of the preservatives such as methyl paraben, propyl paraben, benzalkonium chloride, phenoxyethanol sold under the name phenoxetol by Clariant, benzyl alcohol sold under the name benzyl alcohol by Merck, sodium benzoate sold under the name Probenz SP by Unipex, potassium sorbate sold under the name potassium sorbate by VWR, benzoic acid sold under the name benzoic acid by VWR, 2-bromo-2-nitropropane-1,3-diol sold under the name Bronopol by Jan Dekker International, chlorhexidine sold under the name Chlorexidine digluconate 20% solution by Arnaud Pharmacie, chlorocresol and its derivatives, ethyl alcohol and diazolidinylurea. These preservatives can be used alone or in combination in order to efficiently protect the formulae against any bacterial contamination.

The term "preservative" is intended to mean any substance capable of opposing the modifications of chemical and microbiological origin of a product.

The preservatives preferentially used in the invention are methyl paraben, propyl paraben, benzyl alcohol, phenoxyethanol and potassium sorbate. They can be used at from 0.01% to 5% and preferentially from 0.05% to 2%.

The composition according to the invention may also comprise additives commonly used in the pharmaceutical and cosmetics field for conferring specific properties on said preparation. Those skilled in the art will adapt the choice of these additives according to the expected effect.

Among the additives, mention may be made of, by way of nonlimiting example, taken alone or in combination:
chelating agents such as EDTA (ethylenediaminetetraacetic acid) and its derivatives or salts, dihydroglycerin, citric and tartaric acids, the gluconolactone sold under the name D-(+)-glucono-delta-lactone by Jungbunzlauer, or mixtures thereof,
antioxidants such as vitamin E and its derivatives, for instance DL-alpha-tocopherol or tocopherol acetate from Roche, vitamin C and its derivatives, for instance ascorbyl palmitate from Roche, the butylhydroxytoluene sold under the name Nipanox BHT by Clariant,
soothing agents and/or anti-irritants, such as the PPG-12/SMDI copolymer sold by the company Bertek Pharmaceuticals under the trade name Polyolprepolymer-2, glycerrhetinic acid or its derivatives, for instance Enoxolone sold by the company BASF, hyaluronic acid as it is or in its sodium hyaluronate form sold under the trade name Hyal. Na PWD PH 15-51-45 by the company Contipro, the allantoin sold under the name Ronacare Allantoine by Merck,
any other additives normally used in the pharmaceutical and cosmetics field which make it possible to confer specific properties on said preparation.

The additives will be present in the composition according to the invention in proportions ranging from 0 to 15% and preferentially from 0.1% to 10% by total weight of the composition.

The technology used makes it possible to obtain very fine emulsions; the oil globules obtained have a size predominantly less than 5 μm. The production method consists of two main steps:
The first step consists of the formation of an intermediate "gel" phase; it is an O/W emulsion containing a big proportion of fatty phase and having the appearance of a transparent gel consisting of the active agent, the fatty phase, the sucrose ester, the polyol and water.
The second step consists of the spontaneous dilution of the intermediate "gel" phase in the aqueous phase in order to obtain a very fine oil-in-water emulsion. The final viscosity of the emulsion is dependent on the dilution parameter. The stability of the emulsion can be reinforced by adding a gelling agent.

The production method is particularly sensitive. The speed and the temperature at which certain ingredients are introduced have a significant impact on the physical stability of the emulsions of our invention.

A subject of the present invention is also the method for producing a composition according to the invention.

The general method for producing the "sucrose ester"-based emulsions is described below:
A) Preparation of the "sucrose ester" phase
Solubilize the "sucrose esters" in a part of the purified water and a part of the polyol.
B) Preparation of the fatty/active phase
Solubilize the retinoid in the principal solvent of the active agent, the cosolvent oil(s), the fatty-phase thickener(s) and the mineral oil. Heating the fatty phase during the preparation thereof may be recommended in order to obtain better results.
C) Preparation of the intermediate "gel" phase
The intermediate "gel" phase is obtained by mixing the "sucrose ester" phase and the fatty/active phase.
D) Preparation of the aqueous phase
Add the rest of the polyol and also the other water-soluble additives to the remaining amount of water.
E) Obtaining the cream
The final emulsion is obtained by diluting the intermediate phase with the aqueous phase. Those skilled in the art will know how to adapt this method in order to add thereto the desired ingredients or additives.

The particularly preferred method for producing the "sucrose ester"-based emulsions is described below:
A) Preparation of the "sucrose ester" phase
Solubilize the "sucrose esters" in a part of the purified water and a part of the glycerin.
B) Preparation of the fatty/active phase
Solubilize Compound A in all of the lipophilic ingredients except the benzyl alcohol and the cyclomethicone, which will be added at the end of production.
Heating the fatty phase during the preparation thereof may be recommended in order to obtain better results.
C) Preparation of the intermediate "gel" phase
The intermediate "gel" phase is obtained by mixing the "sucrose ester" phase and the fatty/active phase.
D) Preparation of the aqueous phase
Add the rest of the glycerin and also the other water-soluble additives to the remaining amount of water.

Hyaluronic acid as it is or in its salt form can be added to this phase.

E) Obtaining the cream

The final emulsion is obtained by diluting the intermediate phase with the aqueous phase and by adding the benzyl alcohol, the cyclomethicone and the polyacrylamide-type gelling agent.

A subject of the present invention is also a pharmaceutical composition for use in the treatment of the following pathological conditions:

1) dermatological conditions associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;

2) keratinization disorders, in particular ichthyosis, ichthyosiform conditions, lamellar ichthyosis, Darier's disease, palmoplantar keratoderma, leukoplakia, *pityriasis rubra pilaris* and leukoplakiform conditions, cutaneous or mucosal (buccal) lichen;

3) dermatological conditions with an inflammatory immunoallergic component, with or without a cell proliferation disorder, and in particular all forms of psoriasis, whether cutaneous, mucosal or ungual, and even psoriatic arthritis, or else atopic dermatitis and the various forms of eczema;

4) skin disorders caused by exposure to UV radiation, and also for repairing or combating skin aging, whether it is photo-induced or chronological, or for reducing actinic keratoses and pigmentations, or any pathological conditions associated with chronological or actinic aging, such as xerosis, pigmentations and wrinkles;

5) any condition associated with benign dermal or epidermal proliferations, whether or not they are of viral origin, such as common warts, flat warts, molluscum contagiosum and epidermodysplasia verruciformis, or oral or florid papillomatoses;

6) dermatological disorders such as immune dermatoses, for instance lupus erythematosus, bullous immune diseases and collagen diseases, such as scleroderma;

7) *stigmata* of epidermal and/or dermal atrophy induced by local or systemic corticosteroids, or any other form of cutaneous atrophy;

8) healing disorders, or for preventing or repairing stretch marks, or else for promoting healing;

9) conditions of fungal origin at the cutaneous level, such as tinea pedis and tinea *versicolor;*

10) pigmentation disorders, such as hyperpigmentation, melasma, hypopigmentation or vitiligo;

11) cutaneous or mucosal cancerous or precancerous conditions, such as actinic keratoses, Bowen's disease, in-situ carcinomas, keratoacanthomas and skin cancers such as basal cell carcinoma (BCC), squamous cell carcinoma (SCC) and cutaneous lymphomas such as T lymphoma.

Preferably, the composition is a pharmaceutical composition for use in the treatment of dermatological conditions associated with a keratinization disorder relating to cell differentiation and proliferation, keratinization disorders and dermatological conditions with an inflammatory immunoallergic component, with or without a cell proliferation disorder.

More preferentially, the composition according to the invention is a pharmaceutical composition for use in the treatment of acne, ichthyosis, ichthyosiform conditions, palmoplantar hyperkeratosis or psoriasis.

In accordance with these preferred embodiments, the composition according to the invention preferentially comprises Compound A.

In particular, the composition is preferably a pharmaceutical composition for use in the treatment of acne, which comprises:

a fatty phase comprising from 0.00001% to 1% of 3"-tert-butyl-4'-(2-hydroxyethoxy)-4"-pyrrolidin-1-yl[1,1';3',1"]terphenyl-4-carboxylic acid (compound A); from 0.2% to 5% of principal solvent of compound A; from 0.5% to 60% of oils which are cosolvents of compound A; from 0.5% to 20% of mineral oils; from 0.1% to 10% of fatty-phase thickener; from 0 to 20% of silicone oil;

an aqueous phase comprising from 0.1% to 15% of emulsifiers of the sucrose ester family; from 1% to 40% of polyol; from 0.005% to 10% of aqueous-phase gelling agent;

from 0.01% to 5% of preserving system;

and of from 0.001% to 15% of additives.

Alternatively, the composition is preferably a pharmaceutical composition for use in the treatment of ichthyosis, ichthyosiform conditions, palmoplantar hyperkeratosis or psoriasis, composed:

of a fatty phase comprising from 0.00001% to 1% of 3"-tert-butyl-4'-(2-hydroxyethoxy)-4"-pyrrolidin-1-yl [1,1';3',1"]terphenyl-4-carboxylic acid (compound A); from 0.2% to 5% of solvent of compound A; from 0.5% to 60% of oils which are cosolvents of compound A; from 0.5% to 20% of mineral oils; from 0.1% to 10% of fatty-phase thickener; from 0 to 20% of silicone oil;

of an aqueous phase comprising from 0.1% to 15% of emulsifiers of the sucrose ester family; from 1% to 40% of polyol; from 0.005% to 10% of aqueous-phase gelling agent;

of from 0.01% to 5% of preserving system;

and of from 0.001% to 15% of additives.

I—Formulation Examples

In the following examples, the formulae produced are characterized at T0. The physical and chemical stability of the formulations is determined after storage at ambient temperature (AT) and +40° C. after T+1 Month and/or T+2 Months or T+3 Months or T+6 Months. The material and the methods used for these characterizations are described below.

Chemical Assaying of Compound A:
  Material: HPLC
  Expression of the results: the titer of the active agent is expressed as relative with respect to the initial % performed at T0. The limits set for good stability are 95%-105%.

Macroscopic Observation:
  The macroscopic observation makes it possible to guarantee the physical integrity of the products at T0 and after stability.

Microscopic Observation:
  The microscopic observation makes it possible to evaluate the good solubilization of Compound A as early as T0, the non-recrystallization over time and also the size of the globules of the oily phase.

pH:
  Method: Measurements of the pH carried out at ambient temperature after stabilization of all the samples for 24 h in a chamber at 25° C.

Viscosity:

The viscosity measurement makes it possible to evaluate the consistency of the formulae produced.

Material: Brookfield RV DVII+Pro

Method: Measurements carried out at ambient temperature after stabilization of all the samples for 24 h in a chamber at 25° C. The value is read after 1 minute. The choice of the spindle and of the speed will be described in each composition example. The values obtained are expressed in centipoises (Cps).

Centrifugation:

The centrifugation makes it possible to evaluate the resistance of the formulae to a mechanical stress.

Method: 30 minutes at 5000 rpm

A result which complies signifies that there is neither phase separation nor exudate.

The examples that follow show, in a nonexhaustive manner, examples of formulation of the composition according to the invention and also chemical and physical stability results.

I-1—Examples of Formulae Suitable for Acne:

Examples 1 to 11 can be produced at from 0.001% to 0.03% of compound A.

Example 1

| COMPOSITIONS | | Example 1 |
|---|---|---|
| Trade name | INCI name | % |
| Compound A | N/A | 0.010 |
| GLYCERINE | GLYCERIN | 6.950 |
| SURFHOPE SE PHARMA D-1816 | SUCROSE STEARATE | 0.825 |
| SURFHOPE SE PHARMA D-1616 | SUCROSE PALMITATE | 0.825 |
| PHENOXETOL | PHENOXYETHANOL | 1.000 |
| MIGLYOL812N | CAPRYLIC/CAPRIC TRIGLYCERIDE | 15.000 |
| BENZYL ALCOHOL | BENZYL ALCOHOL | 0.400 |
| POTASSIUM SORBATE | POTASSIUM SORBATE | 0.100 |
| SIMULGEL 600PHA | ACRYLAMIDE/SODIUM ACRYLOYLDIMETHYLTAURATE COPOLYMER ISOHEXADECANE POLYSORBATE 80 | 3.000 |
| RONACARE ALLANTOINE | ALLANTOIN | 0.200 |
| SPEZIOL C16-18 PHARMA | CETYL STEARYL ALCOHOL | 1.980 |
| PRIMOL 352 | MINERAL OIL | 1.750 |
| MARCOL 152 | MINERAL OIL | 1.250 |
| SODIUM HYALURONATE | SODIUM HYALURONATE | 1.750 |
| CYCLOMETHICONE 5NF | CYCLOPENTASILOXANE | 4.000 |
| PURIFIED WATER | N/A | QS 100.000 |

| CHARACTERIZATION AT T0 | MACROSCOPIC APPEARANCE | Soft, white, smooth and shiny cream |
|---|---|---|
| | MICROSCOPIC APPEARANCE | Fine homogeneous covering, Ø ≤ 5 μm |
| | pH | 6.30 |
| | VISCOSITY | Needle 6 Speed 10 67 700 cP |
| | CENTRIFUGATION | Complies |

| Monitoring of stabilities | | | 1 MONTH | 2 MONTHS | 3 MONTHS | 6 MONTHS |
|---|---|---|---|---|---|---|
| Physical stability | pH AT/40° C. | | 6.40/6.01 | 6.40/6.04 | 6.07/5.88 | 5.04/5.06 |
| | Viscosity | AT | 60 500 cP | 58 300 cP | 70 500 cP | 57 400 cP |
| | | 40° C. | 86 000 cP | 68 300 cP | 91 600 cP | 72 400 cP |
| Chemical stability | Amount (% Compound A relative/T0) | AT | 100.4 | 100.8 | 97.8 | 98.2 |
| | | 40° C. | 100.1 | 99.6 | 97.1 | 95.8 |

These results show good physical and chemical stability of the active agent and of the composition as a whole over time.

Example 2

| COMPOSITIONS | | Example 2 |
|---|---|---|
| Trade name | INCI name | % |
| Compound A | N/A | 0.010 |
| VEGETABLE GLYCERINE 4810 | GLYCERIN | 6.950 |
| SURFHOPE SE PHARMA D-1816 | SUCROSE STEARATE | 0.825 |

-continued

| Trade name | INCI name | % |
|---|---|---|
| SURFHOPE SE PHARMA D-1616 | SUCROSE PALMITATE | 0.825 |
| PHENOXETOL | PHENOXYETHANOL | 1.000 |
| MIGLYOL812N | CAPRYLIC/CAPRIC TRIGLYCERIDE | 15.000 |
| NIPAGIN M | METHYLPARABEN | 0.200 |
| NIPASOL M | PROPYLPARABEN | 0.100 |
| SIMULGEL 600PHA | ACRYLAMIDE/SODIUM ACRYLOYLDIMETHYLTAURATE COPOLYMER ISOHEXADECANE POLYSORBATE 80 | 1.200 |
| RONACARE ALLANTOIN | ALLANTOIN | 0.200 |
| SPEZIOL C16-18 PHARMA | CETYL STEARYL ALCOHOL | 1.980 |
| PRIMOL 352 | MINERAL OIL | 1.750 |
| MARCOL 125 | MINERAL OIL | 1.250 |
| CYCLOMETHICONE 5NF | CYCLOPENTASILOXANE | 4.000 |
| PURIFIED WATER | N/A | QS 100.000 |

| CHARACTERIZATION AT T0 | | |
|---|---|---|
| | MACROSCOPIC APPEARANCE | Thick, white, smooth and shiny cream. |
| | MICROSCOPIC APPEARANCE | Fine homogeneous covering, Ø ≤ 5 μm |
| | pH | 5.21 |
| | VISCOSITY | Needle 5 Speed 1 320 700 cP |
| | CENTRIFUGATION | Complies |

| Monitoring of stabilities | | | 1 MONTH | 2 MONTHS | 3 MONTHS | 6 MONTHS |
|---|---|---|---|---|---|---|
| Physical stability | pH AT/40° C. | | 5.23/5.61 | 5.40/5.07 | 5.40/5.08 | 5.19/5.18 |
| | Viscosity | AT | 266 000 cP | 299 000 cP | 307 000 cP | 270 000 cP |
| | | 40° C. | 241 000 cP | 256 000 cP | 253 000 cP | 171 000 cP |
| Chemical stability | Amount (% Compound A relative/T0) | AT | 106.3 | 105 | 106.8 | NR |
| | | 40° C. | 106.5 | 104.8 | 107.6 | NR |

These results show good physical and chemical stability of the active agent and of the composition as a whole over time.

Example 3

| COMPOSITIONS | | Example 3 |
|---|---|---|
| Trade name | INCI name | % |
| Compound A | N/A | 0.010 |
| GLYCERINE | GLYCERIN | 6.950 |
| SURFHOPE SE PHARMA D-1816 | SUCROSE STEARATE | 0.825 |
| SURFHOPE SE PHARMA D-1616 | SUCROSE PALMITATE | 0.825 |
| PHENOXETOL | PHENOXYETHANOL | 1.000 |
| MIGLYOL812N | CAPRYLIC/CAPRIC TRIGLYCERIDE | 15.000 |
| NIPAGIN M | METHYLPARABEN | 0.200 |
| NIPASOL M | PROPYLPARABEN | 0.100 |
| SIMULGEL 600PHA | ACRYLAMIDE/SODIUM ACRYLOYLDIMETHYLTAURATE COPOLYMER ISOHEXADECANE POLYSORBATE 80 | 1.200 |
| RONACARE ALLANTOIN | ALLANTOIN | 0.200 |
| SPEZIOL C16-18 | CETYL STEARYL ALCOHOL | 1.980 |
| PRIMOL 352 | MINERAL OIL | 1.750 |
| MARCOL 152 | MINERAL OIL | 1.250 |
| SODIUM HYALURONATE | SODIUM HYALURONATE | 0.200 |
| CYCLOMETHICONE 5NF | CYCLOPENTASILOXANE | 4.000 |
| PURIFIED WATER | N/A | QS 100.000 |

| CHARACTERIZATION AT T0 | MACROSCOPIC APPEARANCE | Soft, white, smooth and shiny cream |
|---|---|---|
| | MICROSCOPIC APPEARANCE | Fine homogeneous covering, Ø ≤ 5 μm |
| | pH | 5.35 |
| | VISCOSITY | Needle 5 Speed 10 25 240 cP |
| | CENTRIFUGATION | Complies |

| Monitoring of stabilities | | | 1 MONTH | 2 MONTHS | 3 MONTHS | 6 MONTHS |
|---|---|---|---|---|---|---|
| Physical stability | pH AT/40° C. | | 5.34/5.11 | 5.32/5.09 | 5.43/5.17 | 5.41/5.10 |
| | Viscosity | AT | 26 440 cP | 27 400 cP | 28 360 cP | 25 760 cP |
| | | 40° C. | 27 200 cP | 31 600 cP | 28 040 cP | 24 320 cP |
| Chemical stability | Amount (% Compound A relative/T0) | AT | 105.7 | 103.4 | 103.8 | 97 |
| | | 40° C. | 106 | 104.3 | 104.2 | 96 |

These results show good physical and chemical stability of the active agent and of the composition as a whole over time.

Example 4

| COMPOSITIONS | | Example 4 |
|---|---|---|
| Trade name | INCI name | % |
| Compound A | N/A | 0.010 |
| GLYCERINE | GLYCERIN | 6.950 |
| SURFHOPE SE PHARMA D-1816 | SUCROSE STEARATE | 0.825 |
| SURFHOPE SE PHARMA D-1616 | SUCROSE PALMITATE | 0.825 |
| PHENOXETOL | PHENOXYETHANOL | 1.000 |
| MIGLYOL812N | CAPRYLIC/CAPRIC TRIGLYCERIDE | 15.000 |
| NIPAGIN M | METHYLPARABEN | 0.200 |
| NIPASOL M | PROPYLPARABEN | 0.100 |
| SIMULGEL 600PHA | ACRYLAMIDE/SODIUM ACRYLOYLDIMETHYLTAURATE COPOLYMER ISOHEXADECANE POLYSORBATE 80 | 1.200 |
| RONACARE ALLANTOINE | ALLANTOIN | 0.200 |
| SPEZIOL C16-18 PHARMA | CETYL STEARYL ALCOHOL | 1.980 |
| PRIMOL 352 | MINERAL OIL | 1.750 |
| MARCOL 152 | MINERAL OIL | 1.250 |
| POLYVINYL ALCOHOL 40-88 | POLYVINYL ALCOHOL | 0.500 |
| CYCLOMETHICONE 5NF | CYCLOPENTASILOXANE | 4.000 |
| PURIFIED WATER | N/A | QS 100.000 |

| CHARACTERIZATION AT T0 | MACROSCOPIC APPEARANCE | Thick, white, smooth and shiny cream. |
|---|---|---|
| | MICROSCOPIC APPEARANCE | Fine homogeneous covering, Ø ≤ 5 μm |
| | pH | 4.96 |
| | VISCOSITY | Needle 5 Speed 2 133 000 cP |
| | CENTRIFUGATION | Complies |

| Monitoring of stabilities | | | 1 MONTH | 2 MONTHS | 3 MONTHS | 6 MONTHS |
|---|---|---|---|---|---|---|
| Physical stability | pH AT/40° C. | | 5.25/4.96 | 5.35/5.09 | 5.28/5.14 | 5.26/5.06 |
| | Viscosity | AT | 122 000 cP | 113 000 cP | 122 000 cP | 112 000 cP |
| | | 40° C. | 133 000 cP | 121 000 cP | 147 000 cP | 163 000 cP |
| Chemical stability | Amount (% Compound A relative/T0) | AT | 99.2 | 103.7 | 101 | 101.3 |
| | | 40° C. | 98.9 | 103.4 | 97.3 | 106.8 |

These results show good physical and chemical stability of the active agent and of the composition as a whole over time.

Example 5

| COMPOSITIONS | | Example 5 |
|---|---|---|
| Trade name | INCI name | % |
| Compound A | N/A | 0.005 |
| GLYCERINE | GLYCERIN | 6.950 |
| SURFHOPE SE PHARMA D-1816 | SUCROSE STEARATE | 0.825 |
| SURFHOPE SE PHARMA D-1616 | SUCROSE PALMITATE | 0.825 |
| PHENOXETOL | PHENOXYETHANOL | 1.000 |
| MIGLYOL812N | CAPRYLIC/CAPRIC TRIGLYCERIDE | 15.000 |
| NIPASOL M | PROPYLPARABEN | 0.100 |
| NIPAGIN M | METHYLPARABEN | 0.200 |
| SIMULGEL 600PHA | ACRYLAMIDE/SODIUM ACRYLOYLDIMETHYLTAURATE COPOLYMER ISOHEXADECANE POLYSORBATE 80 | 1.200 |
| RONACARE ALLANTOINE | ALLANTOIN | 0.200 |
| SPEZIOL C16-18 PHARMA | CETYL STEARYL ALCOHOL | 1.980 |
| PRIMOL 352 | MINERAL OIL | 1.750 |
| MARCOL 152 | MINERAL OIL | 1.250 |
| SODIUM HYALURONATE | SODIUM HYALURONATE | 0.200 |
| CYCLOMETHICONE 5NF | CYCLOPENTASILOXANE | 4.000 |
| PURIFIED WATER | N/A | QS 100.000 |

| CHARACTERIZATION AT T0 | | |
|---|---|---|
| | MACROSCOPIC APPEARANCE | Thick, white, smooth and shiny cream. |
| | MICROSCOPIC APPEARANCE | Fine homogeneous covering, $\varnothing \leq 5$ μm |
| | pH | 5.45 |
| | VISCOSITY | Needle 5 Speed 20 13 020 cP |
| | CENTRIFUGATION | Complies |

| CHECKS | | | 1 MONTH | 2 MONTHS | 3 MONTHS | 6 MONTHS |
|---|---|---|---|---|---|---|
| Physical stability | pH AT/40° C. | | 5.51/5.51 | 5.59/5.16 | 5.50/5.16 | 5.44/5.41 |
| | Viscosity | AT 40° C. | 13 060 cP | 13 260 cP | 12 580 cP | 13 200 cP |
| | | | 14 300 cP | 14 800 cP | 15 800 cP | 14 760 cP |
| | | | 6 WEEK CHECK | | | |
| Chemical stability | Amount (% Compound A) | AT 40° C. | 100.0 | 106 | 106.7 | |
| | | | 100.1 | 108 | 108.4 | |

These results show good physical and chemical stability of the active agent and of the composition as a whole over time.

Example 6

| COMPOSITIONS | | Example 6 |
|---|---|---|
| Trade name | INCI name | % |
| Compound A | N/A | 0.030 |
| GLYCERINE | GLYCERIN | 6.950 |
| SURFHOPE SE PHARMA D-1816 | SUCROSE STEARATE | 0.825 |
| SURFHOPE SE PHARMA D-1616 | SUCROSE PALMITATE | 0.825 |
| PHENOXETOL | PHENOXYETHANOL | 1.000 |
| MIGLYOL812N | CAPRYLIC/CAPRIC TRIGLYCERIDE | 15.000 |
| NIPAGIN M | METHYLPARABEN | 0.20 |
| NIPASOL M | PROPYLPARABEN | 0.10 |
| SIMULGEL 600PHA | ACRYLAMIDE/SODIUM ACRYLOYLDIMETHYLTAURATE COPOLYMER ISOHEXADECANE POLYSORBATE 80 | 1.200 |

| | | -continued |
|---|---|---|
| RONACARE ALLANTOINE | ALLANTOIN | 0.200 |
| SPEZIOL C16-18 PHARMA | CETYL STEARYL ALCOHOL | 1.980 |
| PRIMOL 352 | MINERAL OIL | 1.75 |
| MARCOL 152 | MINERAL OIL | 1.25 |
| SODIUM HYALURONATE | SODIUM HYALURONATE | 0.200 |
| CYCLOMETHICONE 5NF | CYCLOPENTASILOXANE | 4.000 |
| PURIFIED WATER | N/A | QS 100.000 |

| CHARACTERIZATION AT T0 | MACROSCOPIC APPEARANCE | Thick, white, smooth and shiny cream. |
|---|---|---|
| | MICROSCOPIC APPEARANCE | Fine homogeneous covering, Ø ≤ 5 μm |
| | pH | 5.45 |
| | VISCOSITY | Needle 5 Speed 20 15 480 cP |
| | CENTRIFUGATION | Complies |

| | CHECKS | | 1 MONTH | 2 MONTHS | 3 MONTHS | 6 MONTHS |
|---|---|---|---|---|---|---|
| Physical stability | pH AT/40° C. | | 5.56/5.19 | 5.50/5.47 | 5.52/5.24 | 5.37/5.33 |
| | Viscosity | AT | 15 920 cP | 16 520 cP | 14 400 cP | 15 220 cP |
| | | 40° C. | 13 980 cP | 15 400 cP | 17 860 cP | 13 380 cP |
| | | | 6 WEEK CHECK | | | |
| Chemical stability | Amount (% Compound A) | AT 40° C. | | 98.9 100.1 | 99 99 | 105.3 103 |

These results show good physical and chemical stability of the active agent and of the composition as a whole over time.

Example 7

| COMPOSITIONS | | Example |
|---|---|---|
| Trade name | INCI name | % |
| Compound A | N/A | 0.010 |
| SURFHOPE SE PHARMA D-1816 | SUCROSE STEARATE | 0.500 |
| SURFHOPE SE PHARMA D-1616 | SUCROSE PALMITATE | 0.500 |
| PHENOXETOL | PHENOXYETHANOL | 1.000 |
| MIGLYOL812N | CAPRYLIC/CAPRIC TRIGLYCERIDE | 7.000 |
| REFINED SWEET ALMOND OIL | PRUNUS AMYGDALUS DULCIS (SWEET ALMOND) OIL | 3.500 |
| PRIMOL 352 | MINERAL OIL | 2.000 |
| CYCLOMETHICONE 5NF | CYCLOPENTASILOXANE | 2.000 |
| SPEZIOL C16-18 | CETYL STEARYL ALCOHOL | 3.000 |
| TITRIPLEX III | DISODIUM EDTA | 0.100 |
| GLYCERINE | GLYCERIN | 6.000 |
| BENZOIC ACID | BENZOIC ACID | 0.060 |
| POTASSIUM SORBATE | POTASSIUM SORBATE | 0.060 |
| SIMULGEL 600PHA | ACRYLAMIDE/SODIUM ACRYLOYLDIMETHYLTAURATE COPOLYMER ISOHEXADECANE POLYSORBATE 80 | 3.000 |
| RONACARE ALLANTOIN | ALLANTOIN | 0.200 |
| ASCORBYL PALMITATE | ASCORBYL PALMITATE | 0.020 |
| PURIFIED WATER | N/A | QS 100.000 |

Example 8

| COMPOSITIONS | | Example |
|---|---|---|
| Trade name | INCI name | % |
| Compound A | N/A | 0.010 |
| SURFHOPE SE PHARMA D-1816 | SUCROSE STEARATE | 1.200 |
| SURFHOPE SE PHARMA D-1616 | SUCROSE PALMITATE | 1.200 |
| PHENOXETOL | PHENOXYETHANOL | 0.800 |
| ARLAMOL E | PPG-15 STEARYL ETHER | 10.000 |
| REFINED COCONUT OIL | COCOS NUCIFERA OIL | 2.000 |
| LAUROGLYCOL FCC | PROPYLENE GLYCOL LAURATE | 5.000 |
| MARCOL 152 | MINERAL OIL | 2.000 |
| CYCLOMETHICONE 5NF | CYCLOPENTASILOXANE | 4.000 |
| SPEZIOL C16-18 | CETYL STEARYL ALCOHOL | 2.000 |
| GLYCERINE | GLYCERIN | 6.950 |
| MIGLYOL812N | CAPRYLIC/CAPRIC TRIGLYCERIDE | 15.000 |
| NIPAGIN M | METHYLPARABEN | 0.200 |
| NIPASOL M | PROPYLPARABEN | 0.100 |
| SIMULGEL 600PHA | ACRYLAMIDE/SODIUM ACRYLOYLDIMETHYLTAURATE COPOLYMER ISOHEXADECANE POLYSORBATE 80 | 2.000 |
| RONACARE ALLANTOIN | ALLANTOIN | 0.200 |
| TITRIPLEX III | DISODIUM EDTA | 0.100 |
| PRIMOL 352 | MINERAL OIL | 1.750 |
| SODIUM HYALURONATE | SODIUM HYALURONATE | 0.200 |
| PURIFIED WATER | N/A | QS 100.000 |

Example 9

| COMPOSITIONS | | Example |
|---|---|---|
| Trade name | INCI name | % |
| Compound A | N/A | 0.020 |
| SURFHOPE SE PHARMA D-1816 | SUCROSE STEARATE | 2.300 |
| SURFHOPE SE PHARMA D-1615 | SUCROSE PALMITATE | 2.300 |
| PHENOXETOL | PHENOXYETHANOL | 1.000 |
| MIGLYOL812N | CAPRYLIC/CAPRIC TRIGLYCERIDE | 20.000 |
| Q7-9120 SILICONE FLUID 350 CST | DIMETHICONE | 3.200 |
| SPEZIOL C16-18 | CETYL STEARYL ALCOHOL | 3.000 |
| GLYCERINE | GLYCERIN | 6.950 |
| D-(+)-GLUCONO-DELTA-LACTONE | GLUCONOLACTONE | 0.250 |
| PROBENZ SP | SODIUM BENZOATE | 0.200 |
| SIMULGEL 600PHA | ACRYLAMIDE/SODIUM ACRYLOYLDIMETHYLTAURATE COPOLYMER ISOHEXADECANE POLYSORBATE 80 | 1.200 |
| RONACARE ALLANTOIN | ALLANTOIN | 0.200 |
| PRIMOL 352 | MINERAL OIL | 1.750 |
| SODIUM HYALURONATE | SODIUM HYALURONATE | 0.200 |
| PURIFIED WATER | N/A | QS 100.000 |

Example 10

| COMPOSITIONS | | Example |
|---|---|---|
| Trade name | INCI name | % |
| Compound A | N/A | 0.005 |
| SURFHOPE SE PHARMA D-1816 | SUCROSE STEARATE | 2.000 |
| SURFHOPE SE PHARMA D-1615 | SUCROSE PALMITATE | 2.000 |
| LABRAFIL M1944CS | APRICOT KERNEL OIL PEG-6 ESTER | 2.800 |
| ARLAMOL E | PPG-15 STEARYL ETHER | 6.750 |
| LAUROGLYCOL FCC | PROPYLENE GLYCOL LAURATE | 2.200 |
| PRIMOL 352 | MINERAL OIL | 2.000 |
| Q7-9120 SILICONE FLUID 350 CST | DIMETHICONE | 2.000 |
| SPEZIOL C16-18 | CETYL STEARYL ALCOHOL | 2.000 |
| PHENOXETOL | PHENOXYETHANOL | 0.800 |
| NIPAGIN M | METHYLPARABEN | 0.200 |
| NIPASOL M | PROPYLPARABEN | 0.100 |
| SIMULGEL 600PHA | ACRYLAMIDE/SODIUM ACRYLOYLDIMETHYLTAURATE COPOLYMER ISOHEXADECANE POLYSORBATE 80 | 2.200 |
| RONACARE ALLANTOIN | ALLANTOIN | 0.200 |
| SODIUM HYALURONATE | SODIUM HYALURONATE | 0.200 |
| PURIFIED WATER | N/A | QS 100.000 |

Example 11

| COMPOSITIONS | | Example |
|---|---|---|
| Trade name | INCI name | % |
| Compound A | N/A | 0.030 |
| SURFHOPE SE PHARMA D-1816 | SUCROSE STEARATE | 3.100 |
| SURFHOPE SE PHARMA D-1615 | SUCROSE PALMITATE | 3.100 |
| ARLAMOL PS15E-LQ | PPG-15 STEARYL ETHER | 18.000 |
| REFINED SWEET ALMOND OIL | *PRUNUS AMYGDALUS DULCIS* (SWEET ALMOND) OIL | 2.000 |
| PRIMOL 352 | MINERAL OIL | 2.000 |
| MARCOL152 | MINERAL OIL | 3.000 |
| CYCLOMETHICONE 5NF | CYCLOPENTASILOXANE | 4.000 |
| Q7-9120 SILICONE FLUID 350 CST | DIMETHICONE | 2.000 |
| GLYCERINE | GLYCERIN | 6.950 |
| PHENOXETOL | PHENOXYETHANOL | 1.800 |
| NIPAGIN M | METHYLPARABEN | 0.200 |
| NIPASOL M | PROPYLPARABEN | 0.100 |
| SIMULGEL 600PHA | ACRYLAMIDE/SODIUM ACRYLOYLDIMETHYLTAURATE COPOLYMER ISOHEXADECANE POLYSORBATE 80 | 1.000 |
| RONACARE ALLANTOIN | ALLANTOIN | 0.200 |
| SPEZIOL C16-18 | CETYL STEARYL ALCOHOL | 2.000 |
| ASCORBYL PALMITATE | ASCORBYL PALMITATE | 0.020 |
| SODIUM HYALURONATE | SODIUM HYALURONATE | 0.200 |
| PURIFIED WATER | N/A | QS 100.000 |

I-2—Examples of Formulae Suitable for Ichthyosis, Ichthyosiform Conditions, Palmoplantar Hyperkeratosis or Psoriasis:

Example 12

| COMPOSITIONS | | Example 7 |
|---|---|---|
| Trade name | INCI name | % |
| Compound A | N/A | 0.01 |
| SURFHOPE SE PHARMA D-1816 | SUCROSE STEARATE | 1.50 |
| SURFHOPE SE PHARMA D-1616 | SUCROSE PALMITATE | 1.50 |
| GLYCERINE | GLYCERIN | 14.00 |
| MIGLYOL 812 N | CAPRYLIC/CAPRIC TRIGLYCERIDES | 15.00 |
| PRIMOL 352 | *PARAFFINUM LIQUIDUM* (MINERAL OIL) | 4.50 |
| SPEZIOL C16-18 PHARMA | CETEARYL ALCOHOL | 4.50 |
| REFINED COCONUT OIL | *COCOS NUCIFERA* (COCONUT) OIL | 6.00 |
| REFINED SWEET ALMOND OIL | *PRUNUS AMYGDALUS DULCIS* (SWEET ALMOND) OIL | 15.00 |
| PHENOXETOL | PHENOXYETHANOL | 1.00 |
| BENZYL ALCOHOL | BENZYL ALCOHOL | 0.40 |
| POTASSIUM SORBATE | POTASSIUM SORBATE | 0.10 |
| ALLANTOINE | ALLANTOIN | 0.20 |
| SODIUM HYALURONATE | SODIUM HYALURONATE | 0.20 |
| SIMULGEL 600 PHA | ACRYLAMIDE/SODIUM ACRYLOYLDIMETHYL TAURATE COPOLYMER & ISOHEXADECANE & POLYSORBATE 80 | 1.00 |
| PURIFIED WATER | AQUA (WATER) | QS |

| CHARACTERIZATION AT T0 | | |
|---|---|---|
| MACROSCOPIC APPEARANCE | Thick white cream | |
| MICROSCOPIC APPEARANCE | Covering of emulsion Æ < 3 μm with some globules of greater Æ | |
| pH | 6.63 | |
| VISCOSITY | 1 000 000 cp 50% | |
| CENTRIFUGATION | Complies | |

| Monitoring of stabilities | | | 1 MONTH | 2 MONTHS | 3 MONTHS | 6 MONTHS |
|---|---|---|---|---|---|---|
| Physical stability | pH | AT/40° C. | 6.65/6.15 | 6.47/6.04 | 6.55/6.07 | 6.23/5.79 |
| | Viscosity | AT | 1 110 000 cp 65% | NR | 1 070 000 cp 54% | 1 010 000 cp 52% |
| | | 40° C. | 820 000 cp 41% | NR | 860 000 cp 45% | 760 000 cp 36% |
| Chemical stability | Amount (% Compound A relative/T0) | AT | 100% | 101.4% | 101% | 101.9% |
| | | 40° C. | 101% | 100.8% | 99.6% | 93.4% |

These results show good physical and chemical stability of the active agent and of the composition as a whole over time.

Example 13

| COMPOSITIONS | | Example 8 |
|---|---|---|
| Trade name | INCI name | % |
| Compound A | N/A | 0.01 |
| SURFHOPE SE PHARMA D-1816 | SUCROSE STEARATE | 1.25 |
| SURFHOPE SE PHARMA D-1616 | SUCROSE PALMITATE | 1.25 |
| GLYCERINE | GLYCERIN | 12.50 |
| MIGLYOL 812 N | CAPRYLIC/CAPRIC TRIGLYCERIDES | 15.00 |
| PRIMOL 352 | *PARAFFINUM LIQUIDUM* (MINERAL OIL) | 4.50 |
| SPEZIOL C16-18 PHARMA | CETEARYL ALCOHOL | 2.00 |

| | | |
|---|---|---|
| REFINED COCONUT OIL | *COCOS NUCIFERA* (COCONUT) OIL | 6.00 |
| REFINED SWEET ALMOND OIL | *PRUNUS AMYGDALUS DULCIS* (SWEET ALMOND) OIL | 10.00 |
| PHENOXETOL | PHENOXYETHANOL | 1.00 |
| BENZYL ALCOHOL | BENZYL ALCOHOL | 0.40 |
| POTASSIUM SORBATE | POTASSIUM SORBATE | 0.10 |
| ALLANTOINE | ALLANTOIN | 0.20 |
| SODIUM HYALURONATE | SODIUM HYALURONATE | 0.20 |
| SIMULGEL 600 PHA | ACRYLAMIDE/SODIUM ACRYLOYLDIMETHYL TAURATE COPOLYMER & ISOHEXADECANE & POLYSORBATE 80 | 2.00 |
| PURIFIED WATER | AQUA (WATER) | QS |

| CHARACTERIZATION AT T0 | MACROSCOPIC APPEARANCE | Thick, white, shiny cream |
|---|---|---|
| | MICROSCOPIC APPEARANCE | Covering of emulsion Æ < 3 µm with some globules of 40 µm < Æ < 50 µm |
| | pH | 6.56 |
| | VISCOSITY | 494 000 cp 49.4% |
| | CENTRIFUGATION | Complies |

| Monitoring of stabilities | | | 1 MONTH | 2 MONTHS | 3 MONTHS | 6 MONTHS |
|---|---|---|---|---|---|---|
| Physical stability | pH | AT/40° C. | 6.62/6.30 | 6.80/6.07 | 6.42/5.87 | 6.17/5.84 |
| | Viscosity | AT | 429 000 cp 42.9% | NR | 367 000 cp 36.7% | 348 000 cp 34.8% |
| | | 40° C. | 490 000 cp 49% | NR | 330 000 cp 33% | 345 000 cp 34% |
| Chemical stability | Amount (% Compound A relative/T0) | AT | 96% | 97.3% | 96.1% | 96.3% |
| | | 40° C. | 97% | 97.3% | 96.7% | 95.7% |

These results show good physical and chemical stability of the active agent and of the composition as a whole over time.

II. Cutaneous Penetration on Human Skin

II-1—In Vitro Evaluation Methods

The in vitro tests are developed on glass diffusion cells (termed "Franz cells") or Teflon diffusion cells, in static or dynamic modes. The cells consist of two compartments, a donor compartment and a receiver compartment, separated by a membrane, the orientation of which may be vertical or horizontal.

The membranes have a surface area generally of between 1 and 4 $cm^2$; they can be synthetic (cellulose, polydimethylsiloxane, etc.), but animal or human skin biopsies are preferable.

Samples of receiver liquid can be taken, at regular times over the course of 24 hours, in order to enable the establishment of the kinetics of diffusion through the skin when this proves necessary. At the end of a maximum of 24 h of application, in the case of the pharmaceutical and cosmetic products, the Franz cells are dismantled, and the substance studied is quantified in the following compartments: formulation remains, stratum corneum, epidermidis, dermis, and receiver liquid. The mass balance can in this case be established, which makes it possible to quantify the "absorbed" doses (present in the receiver liquid), the doses "having penetrated" (present in the viable epidermidis and the dermis) and the "nonabsorbed" doses (present in the formulation remains and the stratum corneum).

The study of the kinetics of penetration into the skin makes it possible to provide valuable information regarding the behaviour of the formulae over time and makes it possible to provide the best characterization of the compositions of the formulae.

Two types of cutaneous penetration studies on human skin ex vivo were therefore carried out. In these studies, compound A was tested in the example-1 composition.

II-2—"Single Time" Cutaneous Penetration Study

In this study, the formula is applied for 16 h at the surface of human skin resulting from abdominal surgery, applied in a Franz cell. At the end of the application, compound A is quantified in the various skin compartments: stratum corneum, epidermis, dermis and receiving liquid according to a validated bioanalysis method.

The example-1 composition (sucrose ester emulsion containing 100 µg/g of Compound A) according to the invention is compared with the reference gel, the formula of which consists of: 30% propylene glycol, 67.99% of 95-96% ethanol, 2% Klucel HF, 0.01% compound A.

The bioanalysis was carried out by positive electrospray ionization tandem mass spectrometry, and using a Xevo apparatus (Waters).

The LC/MS/MS conditions developed made it possible to detect up to 0.1% of the dose applied in each of the compartments (dose nonabsorbed, stratum, epidermis, dermis and receiving liquid).

The technical conditions are given in the table below.

In this type of "single point" study, the parameters retained are:
  a. the distribution profile in the various compartments (qualitative data),
  b. the penetration in the epidermis+dermis compartment (numerical data).

a—Distribution Profile in the Various Compartments

The results obtained for the distribution profile of compound A in the various skin compartments are represented by FIG. 1.

FIG. 1 shows that the distribution between the various compartments is of the same order of magnitude for the 2 formulae evaluated.

These data show the preferential localization and an accumulation of compound A in the stratum corneum and, less preferentially, in the epidermis.

b—Values for Penetration in the Epidermis+Dermis Compartment

The penetration values for the emulsion according to the invention containing 100 µg/g (0.01%) of Compound A are between 0.73 ng/cm$^2$ and 1.93 ng/cm$^2$. These values are of the same order of magnitude as for the reference gel.

It can therefore be concluded that compound A is indeed released after application to the skin and penetrates as far as into the epidermis.

II-3—Penetration Kinetics Study

In this type of study, the penetration of the active agent is quantified in each compartment of the skin after 0.5 h, 1 h, 3 h, 6 h and 24 h of application. Kinetics of penetration into each compartment are then determined and characterized.

The example-1 composition (sucrose ester emulsion containing 100 µg/g of Compound A) according to the invention is compared with the reference gel, the formula of which consists of: 30% propylene glycol, 67.99% of 95-96% ethanol, 2% Klucel HF, 0.01% compound A.

The details of the cutaneous application are given in the table below:

| Skin | 3 donors, 2 samples per donor per time, n = 6 |
|---|---|
| Source | Dermatomed abdominal human skin from a corpse |
| Thickness | 500 µm |
| Franz cells | 1-2 cm$^2$ |
| Barrier Function Products | Evaluated using tritiated water |
| Reference gel 100 µg/g | Example-1 emulsion 100 µg/g |
| Application of Formula | ~2 mg/cm$^2$ |
| Amount of active agent applied | Between 100-200 ng/cm$^2$ |
| Exposure time Samples taken up | Up to 24 h |
| Exposure time | 0.5, 1, 3, 6, 24 h |
| Analyses | LC/UV and LC/MS |
| Quantification limit | 15 ng/ml |

The amount of active agent in each compartment at each time was determined by LC/UV or by LC/MS. The bioanalysis method was validated so as to detect at least 0.1% of the dose applied in each compartment.

In this type of study, the parameters retained are:
a. The profile of the kinetics of penetration into the epidermis (qualitative data).
b. The initial rate of the penetration into the epidermis.
c. The maximum amount penetrated into the epidermis.
a. Profile of the Kinetics of Penetration into the Epidermis (FIG. 2)

Figure 2:
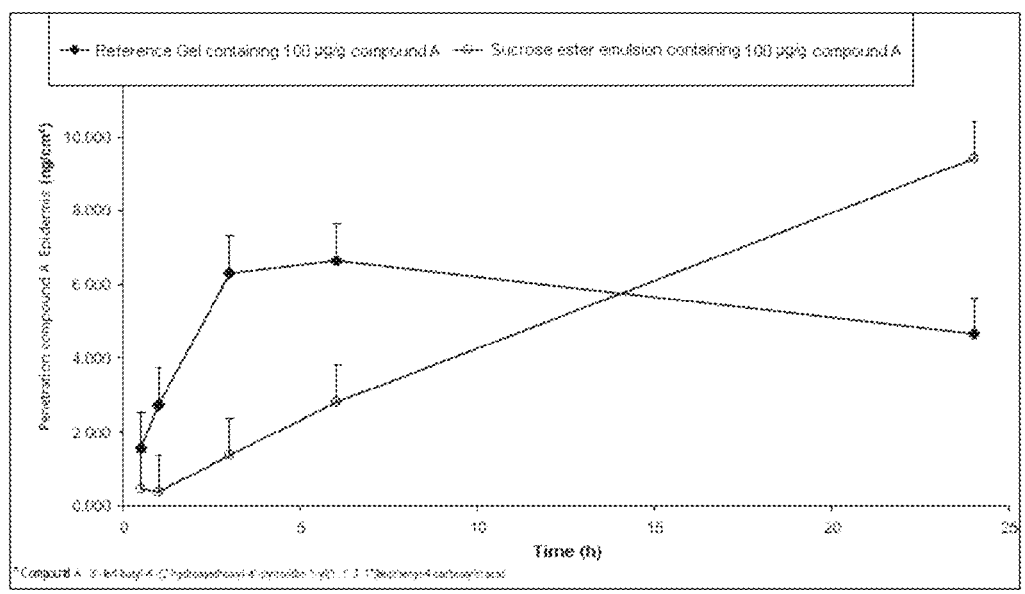
FIG. 2 is the kinetic penetration profile of compound A used with the reference formula (gel) and the emulsion.

The profile of the kinetics of penetration of compound A used with the reference formula (gel) and the emulsion according to the invention is represented in FIG. 2. In particular, FIG. 2 represents the amount of compound A which penetrates into the epidermis as a function of time.

The penetration of compound A obtained for the reference formula (gel) shows conventional kinetics with an accumulation in the compartment during the first hours and subsequently the reaching of a plateau. On the other hand, the penetration kinetics observed after application of the emulsion according to the invention tends to be gradual and linear over time.

As seen in section II.2 ("Single time" cutaneous penetration study), these two formulae have penetration levels at 16 h which are of the same order of magnitude. This kinetics study shows that, even with similar penetration levels in the single time kinetics study, the formula according to the invention exhibits a penetration kinetics profile different than the reference gel, with a gradual accumulation of compound A over time. The application of the emulsion according to the invention therefore made it possible to considerably modify the kinetics of penetration of compound A into the skin. These penetration kinetics are gradual and linear, and are similar to zero order kinetics with reference to the kinetics of diffusion of an active agent through a synthetic membrane or skin after application of a pharmaceutical preparation.

b. Initial Rate of the Kinetics:
The values of the initial rate of the kinetics or slope are between 0.45 ng/cm$^2$/h and 0.54 ng/cm$^2$/h.

c. Maximum Amount Penetrated into the Epidermis:
The maximum amount penetrated into the epidermis is between 9.40 ng/cm$^2$ and 15.50 ng/cm$^2$.

This penetration study showed, unexpectedly, that the formulations according to the invention exhibited specific cutaneous penetration characteristics with kinetics of penetration of compound A into the epidermis tending to be linear, which will make it possible to release the retinoid gradually in the epidermis after application.

II-4. Skin Tolerance

In this study:
10 subjects received 2 grams of reference Gel applied on 1000 cm$^2$ for 4 weeks.
10 subjects received 2 grams of Cream A (example 1 according to the invention) applied on 1000 cm$^2$ for 4 weeks.

During the study, the investigators had the possibility of changing the area of application in the event of excessive irritation.

Figure 3:
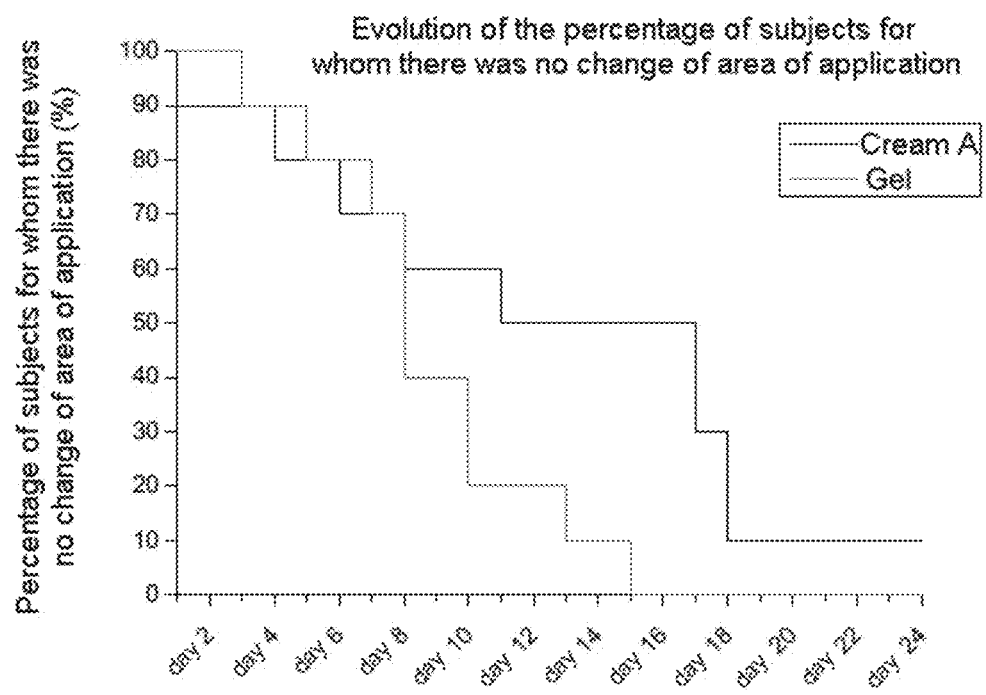
FIG. 3 is a graphical representation of the percentage of subjects for whom there was no change of area of application, as a function of the day of application.

The graph of FIG. 3 represents the percentage of subjects for whom there was no change of area of application, as a function of the day of application.

For example, on the day 5, for 80% of the subjects receiving Cream A, there was no need to change the area of application. In other words, 20% of the subjects having received Cream A showed an irritation requiring a change of area of application.

Evolution of the Percentage of Subjects for Whom there is No Change of Area of Application

| | | Cream A 50 µg/g 1000 cm$^2$ | Gel 50 µg/g 1000 cm$^2$ | Gel 50 µg/g 2000 cm$^2$ | Gel 100 µg/g 1000 cm$^2$ | Gel 25 µg/g 1000 cm$^2$ |
|---|---|---|---|---|---|---|
| Day 2 | N (%) | 1 (10) | — | — | — | — |
| Day 4 | N (%) | — | 1 (10) | — | — | — |
| Day 5 | N (%) | 1 (10) | — | 2 (20) | 1 (10) | — |
| Day 6 | N (%) | — | 1 (10) | — | 1 (10) | — |
| Day 7 | N (%) | 1 (10) | — | 2 (20) | 1 (10) | 1 (10) |

|  |  | Cream A 50 µg/g 1000 cm² | Gel 50 µg/g 1000 cm² | Gel 50 µg/g 2000 cm² | Gel 100 µg/g 1000 cm² | Gel 25 µg/g 1000 cm² |
|---|---|---|---|---|---|---|
| Day 8 | N (%) | — | 1 (10) | — | 2 (20) | 1 (10) |
| Day 9 | N (%) | 1 (10) | 3 (30) | 2 (20) | 1 (10) | — |
| Day 10 | N (%) | — | — | 1 (10) | 1 (10) | 1 (10) |
| Day 11 | N (%) | — | 2 (20) | — | 1 (10) | 1 (10) |
| Day 12 | N (%) | 1 (10) | — | 1 (10) | — | 1 (10) |
| Day 13 | N (%) | — | — | — | — | — |
| Day 14 | N (%) | — | 1 (10) | 2 (20) | 1 (10) | 2 (20) |
| Day 16 | N (%) | — | 1 (10) | — | 1 (10) | — |
| Day 18 | N (%) | 2 (20) | — | — | — | 1 (10) |
| Day 19 | N (%) | 2 (20) | — | — | — | — |
| Day 24 | N (%) | — | — | — | — | 1 (10) |
| No change during the study | N (%) | 1 (10) | — | — | — | 1 (10) |

Thus, it is noted that the irritation appears more rapidly in the individuals who received the reference Gel than in the individuals who received the Cream according to the invention. A clear difference is observed starting from day 9. The composition according to the invention is therefore better tolerated than the reference gel.

The invention claimed is:

1. A pharmaceutical composition of oil-in-water emulsion type comprising:
   a fatty phase comprising at least one active ingredient, wherein the at least one active ingredient is 3"-tert-butyl-4'-(2-hydroxyethoxy)-4"-pyrrolidin-1-yl[1,1';3',1"]terphenyl-4-carboxylic acid, at least one principal solvent of the active ingredient, one or more cosolvent oils, and a mineral oil;
   an aqueous phase comprising at least one surfactant of the sucrose ester family; at least one polyol; and purified water.

2. The composition as claimed in claim 1, wherein the surfactant is selected from the group consisting of sucrose palmitate, sucrose stearate or a mixture thereof.

3. The composition as claimed in claim 1, wherein the aqueous phase comprises at least one gelling agent.

4. The composition as claimed in claim 3, wherein the gelling agent is sodium acryloyldimethyltaurate copolymer/isohexadecane/polysorbate 80.

5. The composition as claimed in claim 1, wherein the at least one principal solvent of the active agent is phenoxyethanol.

6. The composition as claimed in claim 1, wherein the cosolvent oils are selected from the group consisting of caprylic/capric triglycerides, sweet almond oil, propylene glycol monocaprylate, propylene glycol laurate, PPG-15 stearyl ether, sorbitan sesquioleate, and apricot kernel oil PEG-6 ester.

7. The composition as claimed in claim 1, wherein the mineral oil is a liquid paraffin.

8. The composition as claimed in claim 1, wherein the polyol is glycerin.

9. The composition as claimed in claim 1, wherein the composition also comprises a preservative selected from the group consisting of methyl paraben, propyl paraben, benzyl alcohol, phenoxyethanol and potassium sorbate.

10. The composition as claimed in claim 1, wherein the composition also comprises one or more additives.

11. The composition as claimed in claim 1, wherein the composition comprises:
   at least one gelling agent; and
   at least 5% of water.

12. The composition as claimed in claim 1, the composition comprising:
   a fatty phase comprising from 0.00001% to 1% of the at least one active ingredient,
   an aqueous phase comprising:
      from 0.1% to 15% of sucrose esters;
      from 1% to 40% of polyol;
      from 0.005% to 10% of hydrophilic gelling agent;
      at least 5% of water; and
      from 0% to 15% of one or more additives.

13. The composition as claimed in claim 12, wherein the fatty phase also comprises:
   1% of phenoxyethanol;
   1.980% of cetearyl alcohol;
   3% of mineral oils;
   and 15% to 22% of cosolvent oils.

14. The composition as claimed in claim 1, the composition comprising:
   a fatty phase comprising from 0.00001% to 1% of the at least one active ingredient; from 0.1% to 10% of principal solvent of the at least one active ingredient; from 0.5% to 60% of oils which are cosolvents of the at least one active ingredient; from 0.5% to 20% of mineral oils; from 0.1% to 10% of fatty-phase thickener; from 0% to 20% of silicone oil;
   an aqueous phase comprising from 0.1% to 15% of emulsifiers of the sucrose ester family; from 1% to 40% of polyol; from 0.005% to 10% of aqueous-phase gelling agent;
   of from 0.01% to 5% of preserving system;
   and from 0% to 15% of additives.

15. A composition for the treatment of acne, ichthyosis, ichthyosiform conditions, palmoplantar hyperkeratosis or psoriasis, the composition comprising:
   a fatty phase comprising from 0.00001% to 1% of 3"-tert-butyl-4'-(2-hydroxyethoxy)-4"-pyrrolidin-1-yl[1,1';3',1"]terphenyl-4-carboxylic acid (compound A); from 0.2% to 5% of a principal solvent of compound A; from 0.5% to 60% of oils which are cosolvents of compound A; from 0.5% to 20% of mineral oils; from 0.1% to 10% of fatty-phase thickener; from 0% to 20% of silicone oil;

an aqueous phase comprising from 0.1% to 15% of emulsifiers of the sucrose ester family; from 1% to 40% of polyol; and from 0.005% to 10% of aqueous-phase gelling agent;
from 0.01% to 5% of preserving system; and
from 0.001% to 15% of additives.

16. A method of treating a pathological condition, the method comprising administering to an individual subject in need thereof an effective amount of the composition as claimed in claim 1, wherein the pathological condition is selected from the group consisting of:
1) dermatological conditions associated with a keratinization disorder relating to cell differentiation and proliferation;
2) keratinization disorders;
3) dermatological conditions with an inflammatory immunoallergic component, with or without a cell proliferation disorder;
4) skin disorders caused by exposure to UV radiation, and also for repairing or combating skin aging, whether it is photo-induced or chronological, or for reducing actinic keratoses and pigmentations, or any pathological conditions associated with chronological or actinic aging;
5) any condition associated with benign dermal or epidermal proliferations, whether or not they are of viral origin;
6) dermatological disorders such as immune dermatoses and collagen diseases;
7) stigmata of epidermal and/or dermal atrophy induced by local or systemic corticosteroids, or any other form of cutaneous atrophy;
8) healing disorders, or for preventing or repairing stretch marks, or else for promoting healing;
9) conditions of fungal origin at the cutaneous level;
10) pigmentation disorders; and
11) cutaneous or mucosal cancerous or precancerous conditions.

17. The method as claimed in claim 16, wherein the pathological condition is acne.

18. The method as claimed in claim 16, wherein the pathological condition is ichthyosis, ichthyosiform conditions, palmoplantar keratosis or psoriasis.

19. The composition as claimed in claim 1, wherein the composition exhibits zero order penetration kinetics.

20. The composition as claimed in claim 14, wherein the amount of the fatty-phase thickener is from 0.5% to 3%.

21. The composition as claimed in claim 14, wherein the amount of the polyol is from 4% to 10%.

22. The composition as claimed in claim 14, wherein the amount of the additives is from 0.1% to 10%.

23. The method as claimed in claim 16, wherein the dermatological condition associated with a keratinization disorder is selected from the group consisting of common acne, comedonal acne, polymorphic acne, acne rosacea, nodulocystic acne, acne conglobata, senile acne, solar acne, acne medicamentosa and occupational acne.

24. The method as claimed in claim 16, wherein the keratinization disorder is selected from the group consisting of lamellar ichthyosis, Darier's disease, leukoplakia, pityriasis rubra pilaris and leukoplakiform conditions, and cutaneous or mucosal (buccal) lichen.

25. The method as claimed in claim 16, wherein the dermatological condition with an inflammatory immunoallergic component is selected from the group consisting of cutaneous, mucosal, ungual or psoriatic arthritis, atopic dermatitis and eczema.

26. The method as claimed in claim 16, wherein the pathological condition associated with chronological or actinic aging is selected from the group consisting of xerosis, pigmentations and wrinkles.

27. The method as claimed in claim 16, wherein the condition associated with benign dermal or epidermal proliferation is selected from the group consisting of common warts, flat warts, molluscum contagiosum, epidermodysplasia verruciformis, and oral or florid papillomatoses.

28. The method as claimed in claim 16, wherein the dermatological disorder is selected from the group consisting of lupus erythematosus, bullous immune diseases and scleroderma.

29. The method as claimed in claim 16, wherein the condition of fungal origin at the cutaneous level is tinea pedis or tinea versicolor.

30. The method as claimed in claim 16, wherein the pigmentation disorder is selected from the group consisting of hyperpigmentation, melasma, hypopigmentation and vitiligo.

31. The method as claimed in claim 16, wherein the cutaneous or mucosal cancerous or precancerous condition is selected from the group consisting of actinic keratoses, Bowen's disease, in-situ carcinomas, keratoacanthomas and skin cancers.

32. The method as claimed in claim 16, wherein the collagen disease is scleroderma.

33. The method as claimed in claim 31, wherein when the condition is skin cancer, the condition is selected from the group consisting of basal cell carcinoma (BCC), squamous cell carcinoma (SCC) and cutaneous lymphomas.

* * * * *